United States Patent [19]
Koest

[11] Patent Number: 5,870,169
[45] Date of Patent: Feb. 9, 1999

[54] HUMAN EYE VISUAL FIELD TESTING DEVICE

[75] Inventor: Gert Koest, Hannover, Germany

[73] Assignee: Oculus Optikgeraete GmbH, Wetzlar, Germany

[21] Appl. No.: 874,375

[22] Filed: Jun. 19, 1997

[30] Foreign Application Priority Data

Jun. 24, 1996 [DE] Germany .................. 196 25 199.0

[51] Int. Cl.⁶ .................................................. A61B 3/02
[52] U.S. Cl. ........................... 351/225; 351/224; 351/226
[58] Field of Search .................................. 351/225, 224, 351/226, 222, 223, 200, 246

[56] References Cited

U.S. PATENT DOCUMENTS

| | | | |
|---|---|---|---|
| 2,803,990 | 8/1957 | MacKnight | 88/20 |
| 2,837,964 | 6/1958 | Gambs | 88/20 |
| 3,947,099 | 3/1976 | Grolman et al. | 351/35 |
| 4,063,807 | 12/1977 | Gelius et al. | |
| 4,561,738 | 12/1985 | Humphrey et al. | 351/226 |

FOREIGN PATENT DOCUMENTS

| | | |
|---|---|---|
| 2 301 215 | 9/1976 | France . |
| 185 715 | 11/1905 | Germany . |
| 650 912 | 9/1937 | Germany . |
| 227 880A1 | 10/1985 | Germany . |
| 264 664 | 10/1949 | Switzerland . |

*Primary Examiner*—Hung Xuan Dang
*Attorney, Agent, or Firm*—Flynn, Thiel, Boutell & Tanis, P.C.

[57] ABSTRACT

A device for examining the visual field of the human eye which includes a cup-shaped screen, onto the base of which one or several test marks are projected, and usable for both kinetic and also static perimetry testing and offers test marks of a uniform size and brightness over the entire testing area. The screen consists for this purpose of a transparent material, whereby the test marks are projected from the back side onto the screen approximately parallel to the surface normal. The test mark is thereby arranged to move parallel and relative to the back side of the screen, so that each test mark is moved at an equidistant spacing from the screen.

15 Claims, 3 Drawing Sheets

HUMAN EYE VISUAL FIELD TESTING DEVICE

FIELD OF THE INVENTION

The invention relates to a device for testing the visual field of the human eye comprising a cup-shaped screen, onto the base of which one or several test marks are projected.

BACKGROUND OF THE INVENTION

The measurement of the visual field in addition to the measurement of pressure has an important role in the ophthalmology practice. It is known to use the perimeter of Goldmann for measuring the visual field, which perimeter enables the user to carry out both a kinetic-quantitative and also a static-quantitative examination. This kinetic-quantitative perimetry works with a movable test mark of a specific brightness, with which the points of the same contrast sensitivity are located perpendicularly to the visual field limits to be expected or isopters, which is guaranteed by the free mobility of the test mark in every direction. In the static-quantitative perimetry, the patient is offered a stationary test mark with a specific brightness, which is recognized as a superthreshold at any point in the visual field. Both examining methods are as a rule carried out side-by-side so that a device with which both examining methods can be carried out is advantageous.

The Goldmann perimeter is a cup-shaped projection perimeter with a direct registration of the test mark position. The even and constant illumination of the inside of the cup is supposed to guarantee during each examination always the same adaption state of the eye. The test mark, with which one determines the stimulus threshold of the light sensed in the central and peripheral visual field portions, is projected from the cup opening onto the base of the cup. Since, however, the head of the patient is fixed exactly onto the center of the cup, it is compulsory that the projection system is arranged eccentrically. Distortions of varying strength of the test mark in dependency of the respectively chosen test mark position result from this eccentric arrangement. With this not only the shape of the test mark is changed but also its brightness distribution so that sources of error can occur.

SUMMARY OF THE INVENTION

The basic purpose of the invention is to provide a device of the above-identified type in such a manner that this device is suited for both the static and also the kinematic perimetry, which permits to offer test marks of a constant size and constant brightness in the entire testing areas and which moreover is simple in design and operation and furthermore permits an examination of the color vision.

This purpose is attained by a screen consisting of a transparent material, wherein the light source(s) for the test mark(s) is (are) arranged on a swivel arm following the contour of the screen at an equidistant spacing and arranged on its back side remote from the eye being tested, wherein the test mark(s) is (are) projected from the back side onto the screen generally perpendicular to the surface normal, and wherein the light source(s) and thus the test mark(s) is (are) arranged movably flat over its back side.

Thus, a device of the invention consists of a screen made of a transparent material, onto the back side of which the test mark is projected approximately parallel with respect to the surface normal, whereby the light source and thus the test mark is arranged to move parallel and relative to the back side of the screen. The moving of the light source along the back side of the screen occurs approximately with an equidistant spacing from the surface of the screen so that the test mark has always the same size and, through the projection of the test mark parallel to the normal of the screen, has also all over always the same brightness.

The light source for the test marks consist advantageously of one or several LEDs or, however, laser diodes, the light of which is mixed at a specified ratio. This makes it possible to offer the patient a white or, however, any colored test mark. A glass rod is advantageously utilized for the homogenization of the light, on the one end of which glass rod are arranged the diodes. A semitransparent mirror is advantageously arranged between the imaging optics and the light source, through which mirror a reflected beam can be detected to facilitate, for example, an automatic determination and regulation of the brightness of the test mark.

The screen of the device consists advantageously of a light-absorbing or subduing material which has the advantage that light reflected on the inner surface of the screen and covering a great optic distance within the material of the screen before it again comes to the vision side of the screen, is subdued so much that it can no longer be recognized by the patient.

An advantageous design of a device of the invention is that one or several light sources are arranged on a swivel arm, which is constructed corresponding to the curvature of the screen. This swivel arm is rotatable about an axis which extends perpendicular with respect to the projection surface of the screen. The swivel arm must be at least so long that it reaches to the edge of the screen so that upon rotation of the swivel arm same sweeps over the entire screen surface. The light sources required for producing the test marks are arranged on the swivel arm, whereby these can be fixedly or, however, also movably mounted on the swivel arm. The light sources are advantageously arranged fixedly on the swivel arm, whereby the swivel arm as such can be moved relative to its longitudinal axis so that the light sources with their imaging optics are on the one hand movable over half of the periphery of the screen and can by rotating the swivel arm about its swivel axis reach any desired point of the surface of the screen. The spacing of the light sources and of the projection optics from the surface of the screen changes during the movement of the light sources.

The swivel arm is according to an advantageous embodiment held on a mounting plate fastened to the axis of rotation by means of three guide rollers, whereby these guide rollers engage at opposite sides of the swivel arm and are each spaced from one another. Through this it is, on the one hand, possible to move the swivel arm relative to the axis and, on the other hand, it is possible for the swivel arm to always keep its position relative to the screen.

A toothed belt has proven successful as a drive means, which toothed belt is fastened to the ends of the swivel arm and is lifted in the area of its drive pinion from the swivel arm over guide pulleys.

BRIEF DESCRIPTION OF THE DRAWINGS

One exemplary embodiment of the invention will be described in greater detail hereinafter in connection with the drawings in which.

DETAILED DESCRIPTION

Figure 1:
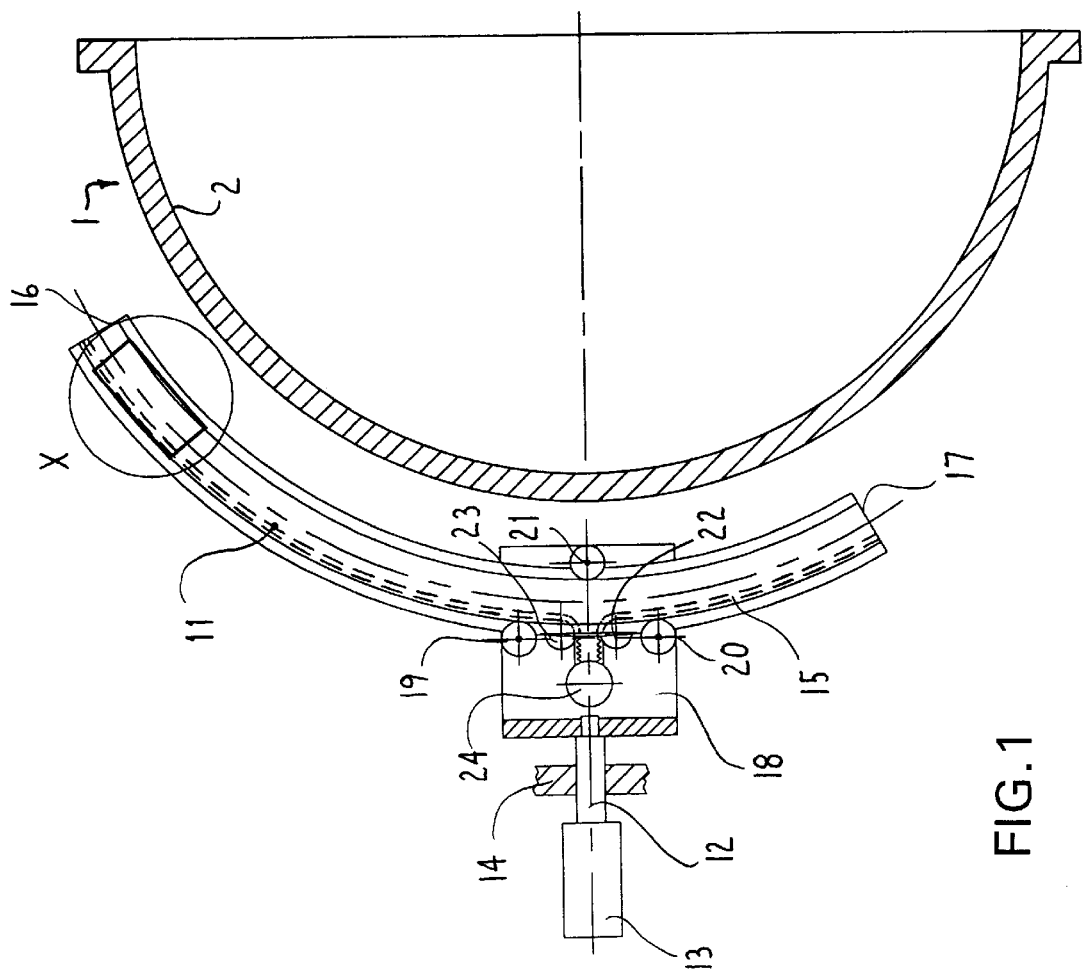
FIG. 1 is a cross-sectional view of the device designed according to the invention.
Figure 2:
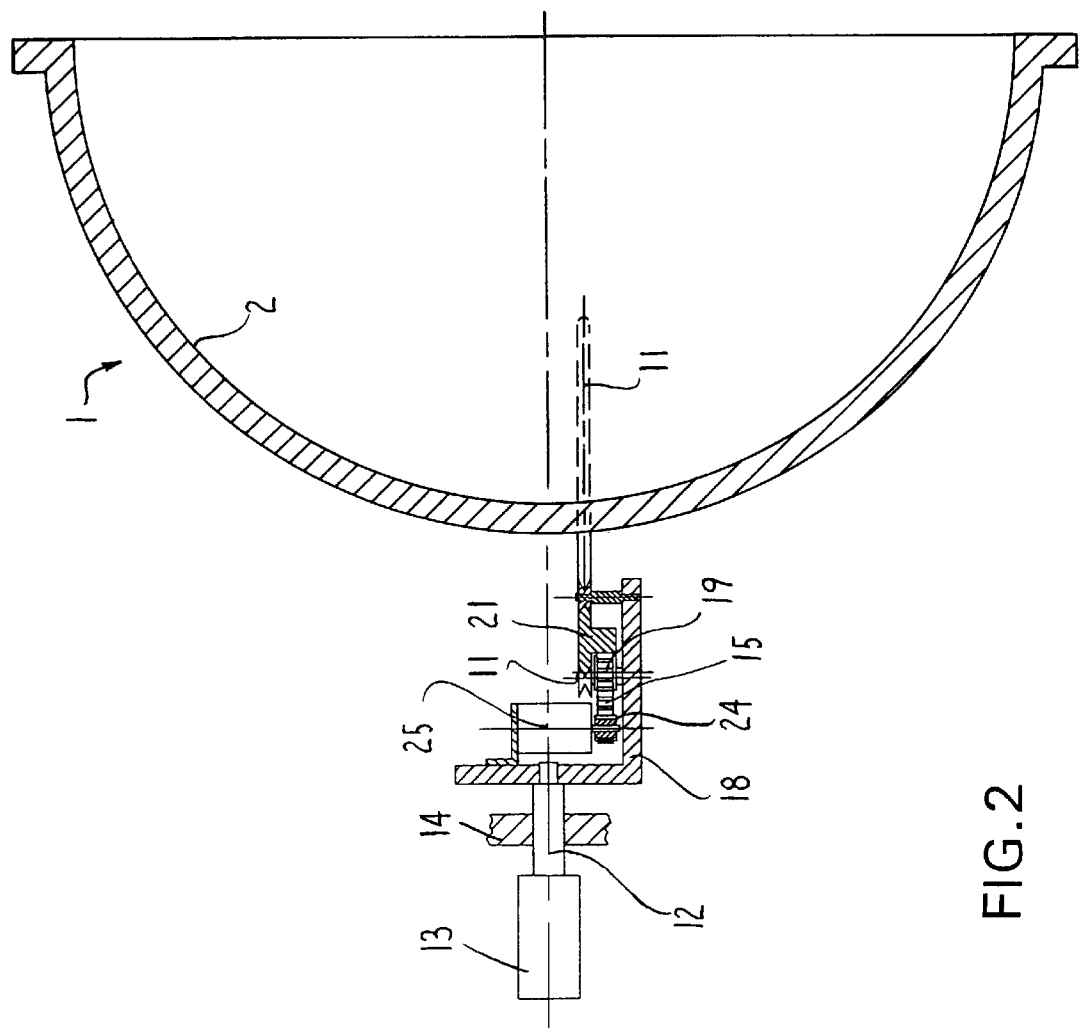
FIG. 2 is a cross-sectional view extending at 90° with respect to FIG. 1.
Figure 3:
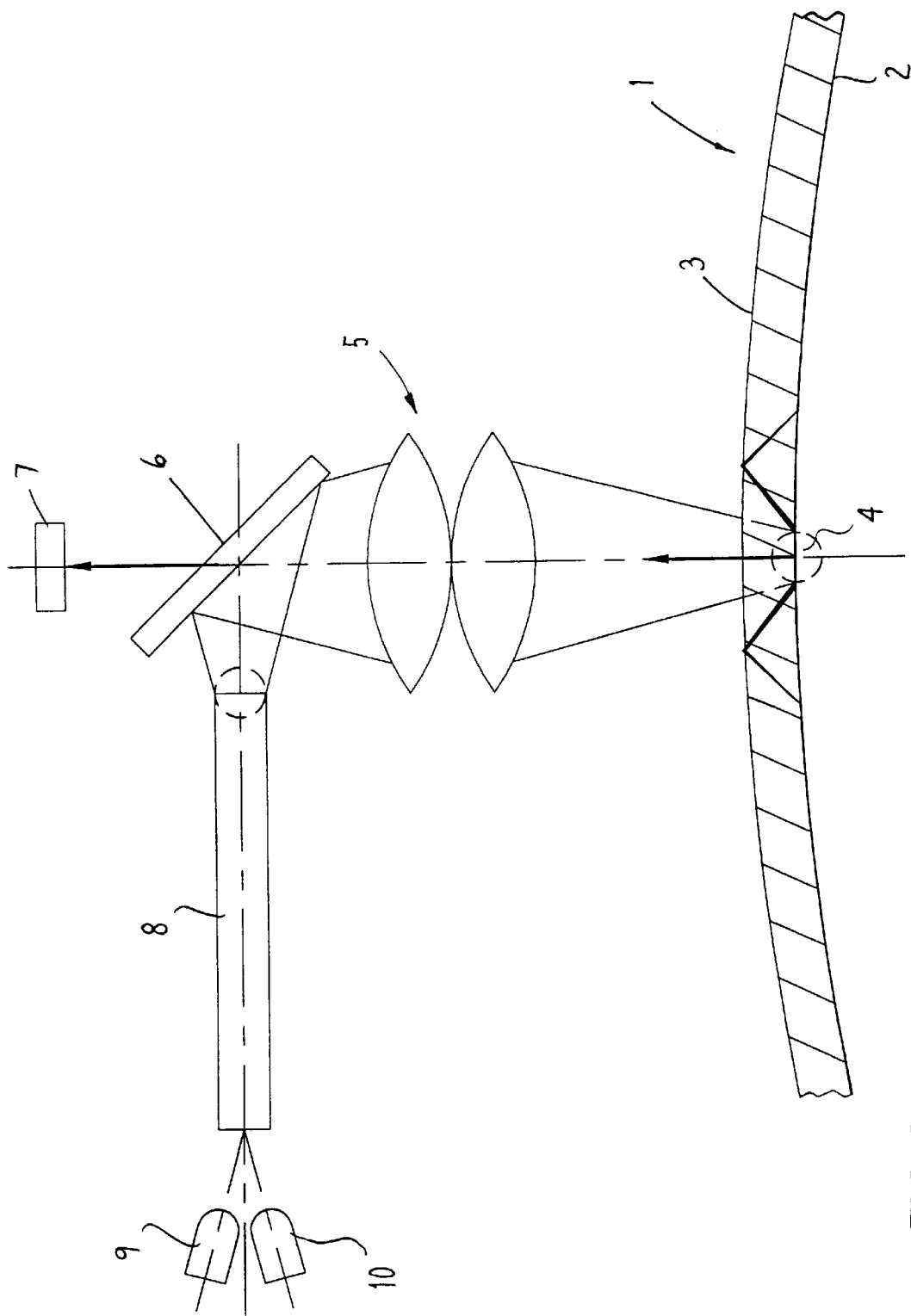
FIG. 3 shows the detail X of FIG. 1 in an enlarged scale.

FIG. 1 illustrates a horizontal cross-sectional view of a perimeter of the invention, whereby the screen 1 is designed hemispherically and has a projection surface 2 on its inner side. The patient looks centrally into the screen, whereby his eye is fixed by a fixation mark not illustrated in the exemplary embodiment. The screen 1 consists of a transparent or translucent material, whereby this material has a relatively great light absorbing or subduing ability so that, as can be seen in FIG. 3, the beams reflected by the test mark 4 are already significantly subdued in their brightness up to the back side 3, where they are again reflected, so that these, when they again hit the front side, namely the projection surface 2 of the screen, are no longer recognized by the eye of the patient. With this it is avoided that the patient sees circular rings on the test mark.

Two diodes 9, 10, which emit their light onto a glass rod 8, are used in order to produce the test mark 4 on the projection surface 2. The light falls from this glass rod onto a semitransparent mirror 6, which is arranged at 45° to the path of the beam. The light is guided from this mirror to the screen 1 through an imaging optics 5, which produces an exactly defined test mark 4. The light reflected by the test mark 4 travels through the semitransparent mirror 6 to a photocell 7, with which the brightness of the reflected light is measured. The measuring signal is utilized for controlling the diodes 9, 10 so that the test mark 4 can be regulated in its brightness precisely to specified values.

The entire imaging optics 5, the semitransparent mirror 6, the photocell 7, the glass rod 8, which is used for the homogenization of the light of the diodes 9, 10, and the diodes 9, 10 are fastened on a swivel arm 11, which is fastened on a mounting plate 18. The swivel arm 11 is supported via three guide rollers 19, 20, 21, two of which engaging one side of the swivel arm 11, the third one engaging the other side as shown in FIG. 1. When the swivel arm 11, which is conformed to the contour of the cup so that same is spaced in all of its areas at an equidistant spacing from the projection surface 2 of the screen 1, is moved, the light source has for producing the test mark 4 always the same spacing from an alignment with respect to the test surface. The swivel arm 11 can be moved within the guide rollers 19, 20, 21 so that the light source unit 9, 10 fixedly arranged on the swivel arm 11 is moved parallel to the screen surface.

In order to effect a simple movement of the swivel arm 11 relative to its guide rollers 19, 20 and 21, a toothed belt 15 is fastened to its ends 16, 17, which belt is lifted off from the swivel arm 11 over two guide pulleys 22, 23 and thence is guided over a drive gear 24 driven by a motor 25.

The swivel arm 11 in turn is fastened on a mounting plate 18, to which are also fastened the guide rollers 19, 20, 21, the guide pulleys 22, 23 and the drive gear 24. The mounting plate in turn is fastened to an axle 12, which is fastened to the frame 14 of the device. This axle is arranged perpendicularly with respect to the projection surface 2 of the screen, namely the extension of the axle runs through the centerpoint of the screen. When this axle 12 is rotated by the motor 13, the light source 9, 10 and thus also the text mark 4 is moved on a circle. By rotating and also by moving the swivel arm 11 relative to the mounting plate 18 and thus to the axle 12, a test mark can be created at any desired point of the projection surface 2 of the screen 1.

The exemplary embodiment illustrates only one light source, however, it is also possible to arrange several light sources on the swivel arm so that light points can also be produced at different points on the screen without shifting of the light source or, however, a rotating of the axle.

The light source 9, 10 consists advantageously of two or three diodes, whereby here either when using two diodes blue and yellow diodes are used or, however, when using three diodes yellow, red and green diodes are used. In order to increase the brightness, the number of the diodes can also be multiplied or, however, laser diodes are used, which can emit an increased light energy. The advantage of using diodes is that by mixing the light of the diodes a white test mark or, however, test marks with any desired colors can be produced on the projection surface. Thus color tests, for example blue perimetry, are possible. Various illnesses, as for example glaucoma, diabetic retinopathy, can be recognized earlier with the blue perimetry and a yellow outer field than is the case with a white test mark.

A known diode system is preferably used as the projection system. Changes in the brightness are advantageously realized through frequency time modulation. Furthermore it is easily possible to offer with the device of the invention different test mark sizes, whereby common test mark sizes have 10 angular minutes or 30 angular minutes.

The fixation of the eye can be achieved in the usual manner through a fixedly installed fixation mark, or, however, a segment image is directly faded in through a CCD camera, whereby the eye to be examined can be positioned precisely to the ball center with a not illustrated adjustable chin support.

It is furthermore by all means possible to arrange additional fixation marks at any desired further points.

It is also possible to use a light fiber line as an alternative to the diode projection system, which light fiber line is fed by a centrally positioned light source. A filter system or a wedge filter can be inserted between the light source and the light conductor in order to effect in a simple manner a suitable brightness gradation. Furthermore, a shutter system can be provided in order to be able to offer the test mark illustration at time intervals.

Both kinetic and also static eye examinations can be carried out with the device of the invention also in the same manner as is the case with the Goldmann perimeter so that values found with the perimeter by the invention can be compared exactly with the values found with the Goldmann perimeter.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In a device for examining the visual field of the human eye comprising a cup-shaped screen, onto the base of which at least one test mark is projected, wherein the screen consists of a transparent material, wherein at least one light source for said at least one test mark is arranged on a swivel arm following the contour of the screen at an equidistant spacing and arranged on its back side remote from the eye being tested, wherein said at least one test mark is projected from the back side onto the screen generally perpendicular to the surface normal, and wherein said light source and thus said at least one test mark is arranged movably flat over its back side, the improvement wherein the screen consists of a light-absorbing material for subduing light passing therethrough from the light source.

2. The device according to claim 1, wherein at least one LED or laser diode is used as the light source for the test mark.

3. The device according to claim 2, wherein either blue and yellow diodes or yellow, red and green diodes are used, which each illuminate one test mark.

4. The device according to claim 3, wherein the diodes are constructed individually controllable for producing the mixed light.

5. The device according to claim 2 wherein for mixing the light starting out from the diodes a glass rod is used.

6. The device according to claim 5, wherein the glass rod has a diameter of approximately 2 cm.

7. The device according to claim 1 wherein the swivel arm is rotatable about an axle which extends perpendicular with respect to the projection surface of the screen.

8. The device according to claim 7, wherein the swivel arm is movable parallel with respect to the projection surface of the screen.

9. The device according to claim 8, wherein the swivel arm is guided by at least three guide rollers which are fastened on a mounting plate connected to the axle of rotation.

10. The device according to claim 9, wherein a toothed belt is arranged on the swivel arm, which toothed belt is fastened to the respective end of the swivel arm, and wherein the toothed belt is guided over two guide pulleys and a drive gear.

11. The device according to claim 7, wherein the light source is movable on the swivel arm.

12. The device according to claim 1, wherein the screen is coated on its inner side.

13. The device according to claim 1, wherein at least one fixation mark is provided in the screen.

14. The device according to claim 1, wherein a partially transparent mirror is arranged in a projection beam for said at least one test mark, and wherein a partially reflected beam portion is detected in its light intensity and is used to control the brightness of said at least one test mark.

15. The device according to claim 14, wherein partially transparent mirror is arranged on the swivel arm.

* * * * *